(12) United States Patent
Mack et al.

(10) Patent No.: US 7,651,515 B2
(45) Date of Patent: Jan. 26, 2010

(54) IMPLANT FOR CORRECTION AND STABILIZATION OF THE SPINAL COLUMN

(75) Inventors: Thomas Mack, Dornstadt (DE); Nikolas Willmann, Ulm (DE); John Sutcliff, Good Easter (GB); Marcus Richter, Eichingen (DE)

(73) Assignee: Ulrich GmbH & Co. KG, Ulm (DE)

( * ) Notice: Subject to any disclaimer, the term of this patent is extended or adjusted under 35 U.S.C. 154(b) by 932 days.

(21) Appl. No.: 10/869,299

(22) Filed: Jun. 16, 2004

(65) Prior Publication Data

US 2004/0267260 A1    Dec. 30, 2004

(30) Foreign Application Priority Data

Jun. 16, 2003    (DE)    ................. 103 27 358

(51) Int. Cl.
*A61B 17/70* (2006.01)
(52) U.S. Cl. ............................ 606/254; 606/907
(58) Field of Classification Search .................. 606/60, 606/246–279, 907; 403/206, 177
See application file for complete search history.

(56) References Cited

U.S. PATENT DOCUMENTS

| | | | | |
|---|---|---|---|---|
| 190,582 | A | * | 5/1877 | Hansell ........................... 267/4 |
| 1,429,146 | A | * | 9/1922 | Karge ............................ 464/58 |
| 3,977,397 | A | * | 8/1976 | Kalnberz et al. ............... 606/57 |
| 5,180,393 | A | * | 1/1993 | Commarmond .......... 623/13.14 |
| 5,672,175 | A | * | 9/1997 | Martin ...................... 606/86 A |
| 2003/0109880 | A1 | * | 6/2003 | Shirado et al. ................. 606/61 |
| 2003/0220643 | A1 | * | 11/2003 | Ferree ........................... 606/61 |
| 2004/0049190 | A1 | * | 3/2004 | Biedermann et al. ........... 606/61 |
| 2004/0236327 | A1 | * | 11/2004 | Paul et al. ....................... 606/61 |
| 2005/0065514 | A1 | * | 3/2005 | Studer ........................... 606/61 |
| 2005/0085815 | A1 | * | 4/2005 | Harms et al. ................... 606/61 |
| 2005/0171543 | A1 | * | 8/2005 | Timm et al. .................... 606/61 |
| 2005/0203519 | A1 | * | 9/2005 | Harms et al. ................... 606/61 |
| 2006/0036240 | A1 | * | 2/2006 | Colleran et al. ............... 606/61 |
| 2006/0142758 | A1 | * | 6/2006 | Petit ............................. 606/61 |

FOREIGN PATENT DOCUMENTS

| | | |
|---|---|---|
| DE | 41 10 002 | 5/1992 |
| EP | 1 281 364 | 2/2003 |
| FR | 2 718 946 | 10/1995 |
| FR | 2 726 995 | 5/1996 |
| FR | 2 799 949 | 4/2001 |
| GB | 2 382 304 | 5/2003 |
| WO | 2004 024011 | 3/2004 |
| WO | WO 2004/105577 | 12/2004 |

OTHER PUBLICATIONS

European Search Report dated Sep. 1, 2004.
European Search Report dated May 5, 2008 with English translation.

* cited by examiner

*Primary Examiner*—Thomas C Barrett
*Assistant Examiner*—James L. Swiger
(74) *Attorney, Agent, or Firm*—Collard & Roe, P.C.

(57) ABSTRACT

An implant for the correction and stabilization of the spinal column, comprising pedicle screws that can be screwed into the vertebrae of a spine, and of at least one connection element that connects the pedicle screws at the screw heads. This connection element is formed by a spiral whose spiral windings are arranged offset in the axial direction, following a screw line.

14 Claims, 3 Drawing Sheets

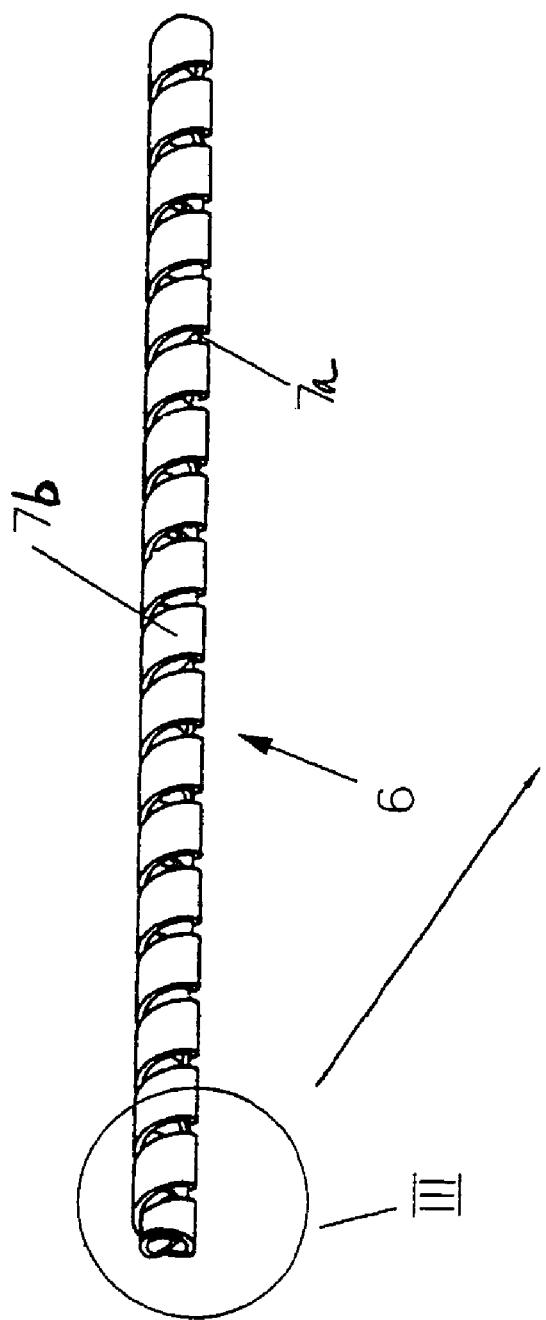
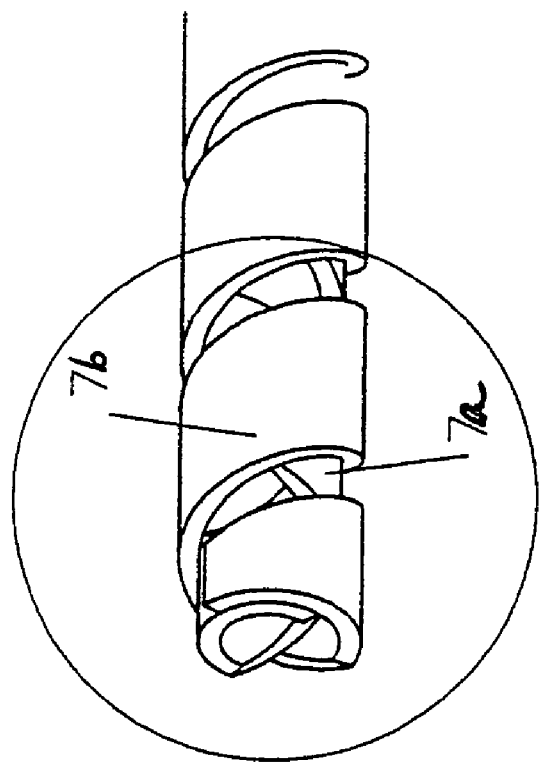

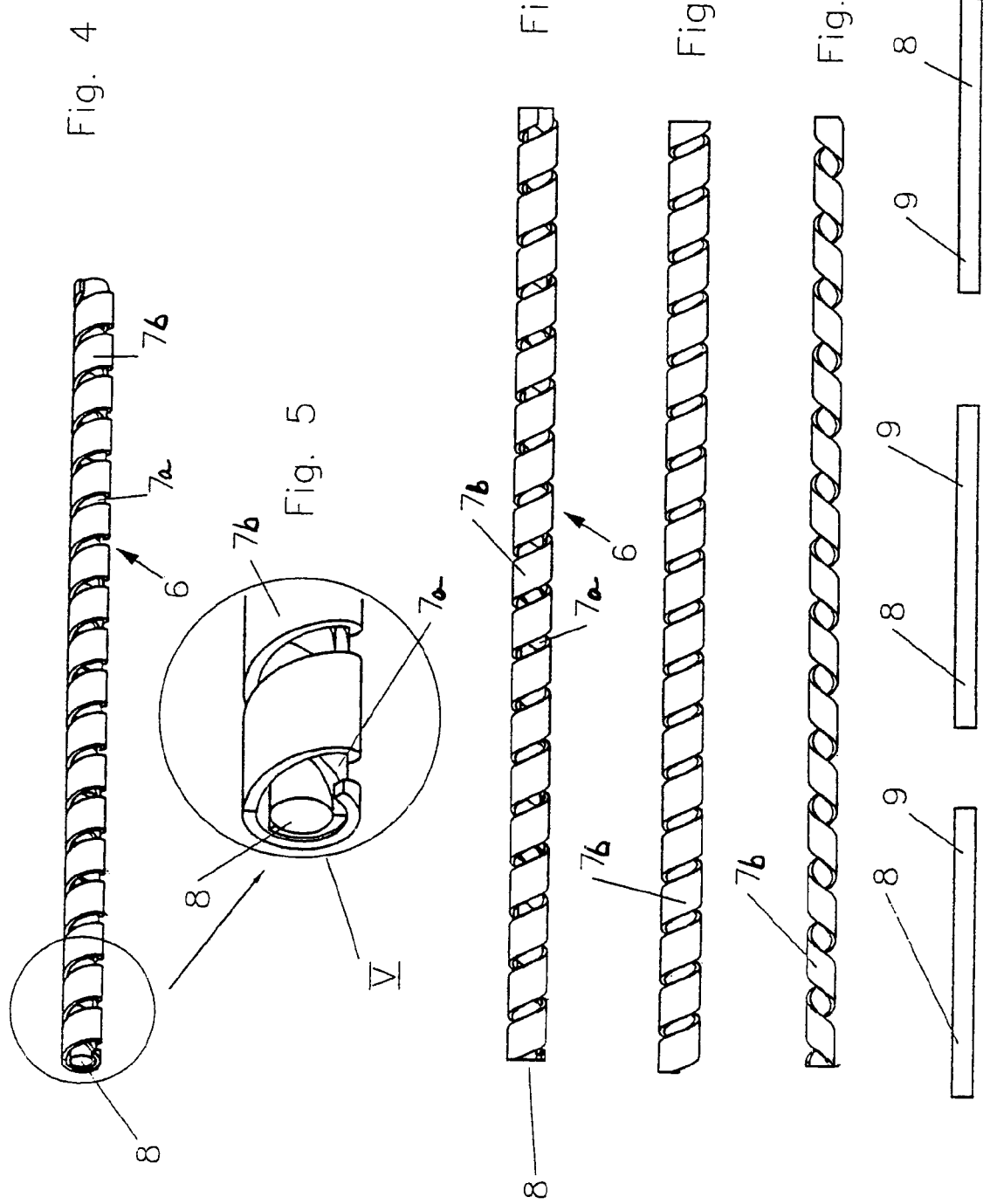

IMPLANT FOR CORRECTION AND STABILIZATION OF THE SPINAL COLUMN

BACKGROUND OF THE INVENTION

The invention relates to an implant for the correction and stabilization of a spinal column, comprising pedicle screws that can be screwed into the vertebrae, and at least one connection element that connects the pedicle screws at screw heads on the pedicle screws.

Spinal implants are known and described, for example, in German Patent No. DE 41 10 002 C1. In this reference there is an implant, wherein the connection element is formed by a metal rod that is fixed in place on the spinal column, using the pedicle screws. This occurs over the length of at least two adjacent vertebrae, to correct and stabilize the spinal column. This is achieved by pushing the vertebrae into a specific spatial position and fixing or forcing them in place. This act results in a stiffening of the spinal column in a specific region, which guarantees that the spinal column can perform its supporting function, even if individual vertebrae or disks in the intervertebral space have been traumatically damaged or have become degeneratively diseased. In the region of the spinal column stiffened by the implant, the natural mobility of healthy vertebra is prohibited, so that adjacent regions of the spinal column are subjected to greater stress, and therefore are more susceptible to wear and friction wear, in other words more degenerative diseases.

SUMMARY OF THE INVENTION

The invention is designed to develop an implant so that after its implantation, there is a greater approximation to the physiological mobility possibilities of a healthy spinal column.

This task is accomplished, by creating a connection element that is formed by a spiral whose spiral windings are arranged offset in the axial direction, following a screw line.

This configuration has the advantage, in that the connection element continues to stabilize the spinal column, and at the same time, even limited mobility of the spinal column is made available, even in the stabilized region. This mobility is because of the spring property that intrinsically results from the shape of the connection element, which allows better physiological adaptation of the stabilized region to the healthy adjacent regions. Particularly, in the case of forces acting on the stabilized region in a pulse-like manner, this region can absorb the forces as a result of the connection element that is configured as a spiral, by means of deflection of the spiral, and subsequently return to its rest position again. This occurs after the forces have been passed off by way of more extensive regions of the spinal column.

In a preferred embodiment, a spiral core is arranged along the interior of the spiral, over at least a partial region of its axial expanse. This spiral core is utilized to influence the spring constant, i.e. the bending stiffness of the spiral, so that this allows the spiral to extend over the region of several vertebrae. In this region there is an increased stiffness of the spiral which is made available only in a limited region, by utilizing the spiral core. Thus, the spiral core can be configured as a rod, whereby the rod is comprised of metal, particularly titanium or surgical steel. In addition, it is possible for the rod to be formed in several parts, from several rod segments, which demonstrate differences in their material properties, particularly in their bending stiffness. This results in the possibility of using different spiral cores. In addition, it is also possible to use spiral cores made of different material, such as metal or plastic, and thereby locally modifying the properties that result from the shape and the material of the spiral, particularly the bending stiffness.

In a preferred embodiment of the invention, there are two spirals wherein one of the spirals is arranged inside the spiral interior of the other spiral. In this embodiment, there is a simplification of the handling of the connection element during operation, whereby, in turn, there is a change in the bending stiffness of the isolated first spiral.

To insert the second spiral into the spiral interior of the first spiral, the direction of rotation of the windings of the two spirals can extend in opposite directions. In this embodiment, the spring effect of the two spirals is also maintained, and there is no risk that the two spirals, with their windings, complement one another to form a pseudo-cylinder.

In addition, with this dual spiral design, with the embodiment in which a second spiral is arranged in the spiral interior of the first spiral, it is also possible to use the spiral core, wherein the spiral core is arranged in the spiral interior of the second spiral, over at least a partial region of its axial expanse.

There is at least one holder for a simple connection of the spiral with the pedicle screws. These holders are assigned to the screw heads of the pedicle screws, for insertion of the spirals, which have clamping means for securing the spirals in the holders. With the configuration of the spirals according to the invention, it is possible to secure these spirals in the holders with the clamping means not only by a non-positive lock, but it can also be designed so that the clamping means are formed by clamping screws that engage with a positive lock through two adjacent spiral windings.

It is also practical to form the spiral as a flat wire spiral. As compared with a round material, this offers the advantage that with a comparatively small diameter of the spiral, there is a greater axial expanse of the spiral, which promotes its function as a connection element between pedicle screws. In view of the intended purpose of use, it is evident that the spiral can be made from titanium or surgical steel.

To achieve the complex and multi-faceted function of the implant with the spiral while still maintaining a sufficient stabilization of the spinal column, along with a sufficient mobility, the flat wire can be made with a material thickness from 0.4 mm to 2.8 mm, preferably 1.2 mm. To promote the function of the spiral, the flat wire can have a material width of 2 mm to 8 mm, preferably 4 mm to 6 mm. With regard to the inside diameter, the dimensions are selected so that the inside diameter has a size of 2.5 mm to 7.5 mm, preferably 3.2 to 4.6 mm. To make damping available, if there is stress on the spiral in its axial direction, adjacent spiral windings have a distance of 0.5 mm to 2.5 mm from one another.

With a spiral for use in the spiral interior of the outer spiral, the distance between adjacent spiral windings is selected to be greater than in the case of the outer spiral, whereby it also becomes clear that the second spiral is merely intended to support the outer spiral.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views:

FIG. 2 is a perspective, isolated representation of the connection element of the implant from FIG. 1;

FIG. 3 is the detail III from FIG. 2;

FIG. 4 is a representation of a connection element having a spiral core inserted into the inner spiral, corresponding to FIG. 2;

FIG. 5 is the detail V from FIG. 4;

FIG. 6 is a side view of the connection element from FIG. 4;

FIG. 7 is a representation of the outer spiral formed as a flat wire spiral, corresponding to FIG. 6;

FIG. 8 is a representation of the inner spiral formed as a flat wire spiral, corresponding to FIG. 6; and FIG. 9 is a side view of the spiral core, structured in several parts.

DETAILED DESCRIPTION

Figure 1:
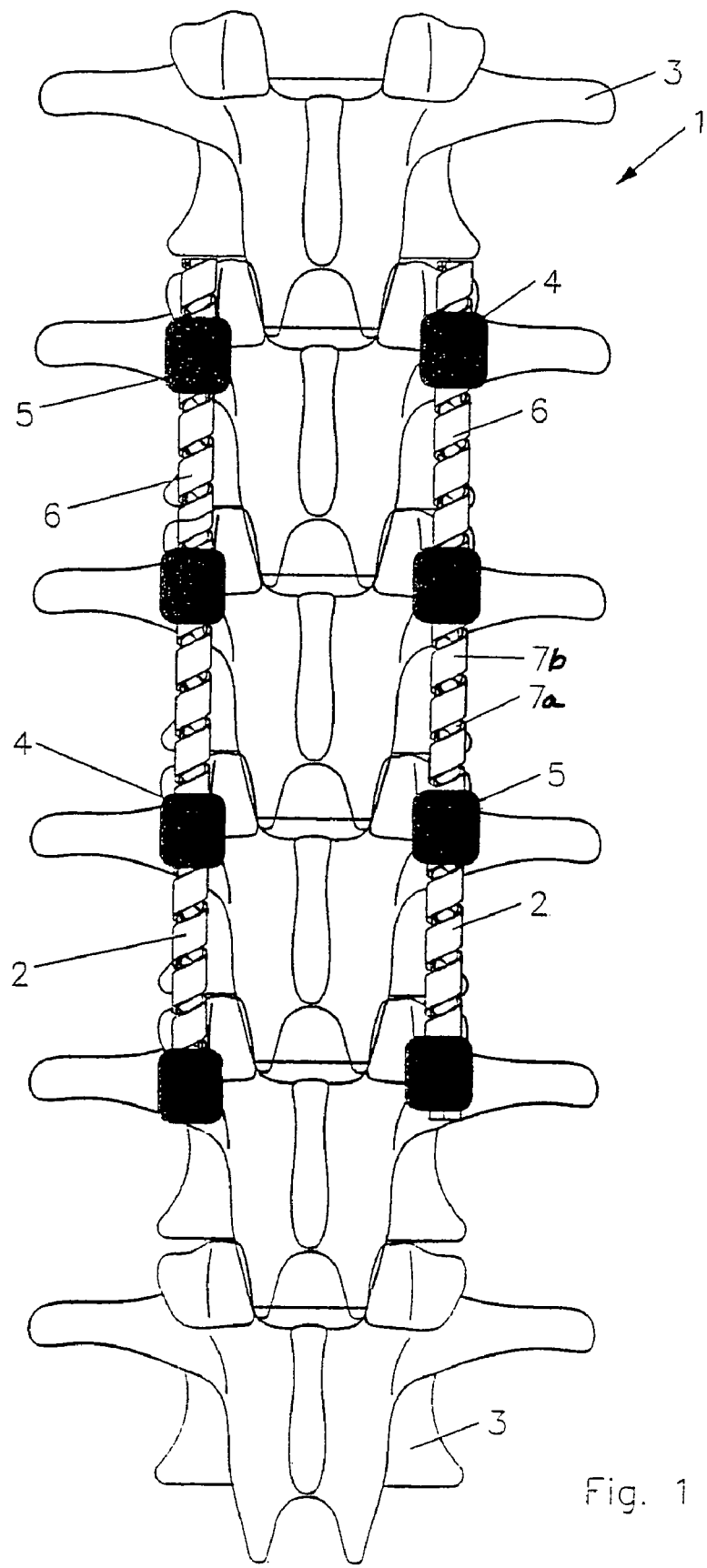
FIG. 1 is a schematic representation of two implants attached to the spinal column, symmetrically to the longitudinal axis of the latter.

Referring to the drawings, FIG. 1 shows a spinal column 1, which is supported in its function via two implants 2, which are used to correct and stabilize spinal column 1. These implants 2 help to hold the individual vertebrae 3 of the spinal column 1 in their anatomically correct position. Each implant 2 comprises several pedicle screws 4, as shown in the exemplary embodiment shown, as well as a connection element 6 that connects pedicle screws 4 at their screw heads 5.

Connection element 6 is formed by one or more spirals which can include an inner spiral 7a and an outer spiral 7b. The spiral windings of these spirals are arranged offset in the axial direction, following a screw line, whereby adjacent spiral windings have a distance of 0.5 mm to 2.5 mm from one another. FIG. 1 shows an example of a design that relates to the invention, in which a material thickness of 1.2 mm was chosen for the flat wire, from a range of 0.4 mm to 2.8 mm, as well as a material width of 6 mm, from a range of 2 mm to 8 mm. The diameter of the winding, for example, the inside diameter of the spiral 7, lies in the range of 2.5 mm to 7.5 mm.

FIGS. 2 and 3 show a more detailed view of connection element 6 which can include two spiral windings 7a and 7b. In particular, FIG. 3 shows a close up view of both inner spiral 7a and outer spiral 7b, with outer spiral 7b wrapping around inner spiral 7a in an opposite rotational direction.

In the embodiment shown in FIGS. 4 to 9, a spiral core 8 is arranged in the interior of spirals 7a and 7b, over at least a partial region of its axial expanse, which is structured as a rod that in turn is composed in several parts, of several rod segments 9 as shown in FIG. 9. This design, includes several rods which demonstrate differences in their material properties, particularly in their bending stiffness.

For example, the rod shown in FIG. 9 can be configured as a spiral core 8 having a center rod segment 9 made of metal, particularly titanium or surgical steel, while the outer rod segments 9 consist of plastic. This design allows the connection element 6 and the implant 2 as a whole to have varied properties, and thereby create regions having a greater stiffness, or greater mobility, by means of a suitable selection of the spiral core 8. This feature is present even if the fundamental determination of the basic properties has already taken place by means of the sizing of the flat wire.

Both the exemplary embodiment in FIGS. 2 and 3 and in FIGS. 5 to 9 show a constellation in which there are two spirals wherein one spiral 7a is arranged in the spiral interior of the other spiral 7b, whereby the direction of rotation of the windings of the two spirals 7a and 7b run in the opposite direction. Because of the fundamentally similar configuration of the outer spiral 7b and the inner spiral 7a, it is also possible to arrange the spiral core 8 in the spiral interior of inner spiral 7a.

The pedicle screws 4, which are shown only schematically in the drawing in FIG. 1, have holders that are assigned to their screw heads 5. A clamping means for securing spirals 7a and 7b in the holders is assigned to screwheads 5. This clamping means may be clamping screws that engage between two adjacent spiral windings, with a positive lock. The result is that there is an improved securing of the spirals 7a and 7b, in other words of the connection element 6 between two pedicle screws 4, to prevent displacement in the axial direction.

Accordingly, while a few embodiments of the present invention have been shown and described, it is to be understood that many changes and modifications may be made thereunto without departing from the spirit and scope of the invention as defined in the appended claims.

What is claimed is:

1. An implant for the connection and stabilization of a spinal column having vertebra, the implant comprising:
   a) a plurality of pedicle screws each having at least one screw head wherein said plurality of pedicle screws is capable of being screwed into the vertebra; and
   b) at least one connection element formed over its entire axial expanse by at least two spirals, each spiral having spiral windings, wherein said spiral windings are arranged offset in an axial direction following a screw line, wherein said at least one connection element connects at least one of said plurality of pedicle screws to an adjacent one of said plurality of pedicle screws, wherein an inner spiral of said at least two spirals is arranged inside a spiral interior of an outside spiral of said two spirals, wherein a direction of rotation of the windings of said at least two spirals is in opposite directions; and
   c) a spiral core which is arranged in an interior of said inner spiral over at least a partial region of its axial expanse, wherein said spiral core is configured as a titanium rod formed from multiple segments, and wherein at least two of said rod segments have at least two different material properties at least in the form of bending stiffness.

2. The implant as in claim 1, further comprising a plurality of holders which are coupled to said screw heads of said plurality of pedicle screws, wherein said plurality of holders are for allowing an insertion of said at least two spirals, which have clamping means for securing said at least two spirals in said plurality of holders.

3. The implant according to claim 1, wherein said at least two spirals are formed as flat wire spirals.

4. The implant according to claim 3, wherein said at least two spirals are made from titanium.

5. The implant as in claim 3, wherein said at least two spirals are made from surgical grade steel.

6. The implant according to claim 3, wherein said flat wire has a material thickness from 0.4 mm to 2.8 mm.

7. The implant according to claims 3, wherein said flat wire has a material thickness of 1.2 mm.

8. The implant according to claim 3, wherein said flat wire has a material width of 2 mm to 8 mm.

9. The implant according to claim 3, wherein said flat wire has a material width of 4 mm to 6 mm.

10. The implant according to claim 3, wherein an inside diameter of said spiral has a size of between 2.5 mm to 7.5 mm.

11. The implant according to claim 3, wherein an inside diameter of said spiral has a size of between 3.2 and 4.6 mm.

12. The implant according to claim 3, wherein adjacent spiral windings have a distance of 0.5 mm to 2.5 mm from one another.

13. The implant according to claim 1, wherein a distance between adjacent spiral windings of said inner spiral is selected to be greater than in the case of the outer spiral.

14. The implant as claimed in claim 1, wherein said rod is formed from surgical grade steel.

* * * * *

UNITED STATES PATENT AND TRADEMARK OFFICE
CERTIFICATE OF CORRECTION

PATENT NO. : 7,651,515 B2 Page 1 of 1
APPLICATION NO. : 10/869299
DATED : January 26, 2010
INVENTOR(S) : Mack et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1311 days.

Signed and Sealed this

Twenty-third Day of November, 2010

David J. Kappos
*Director of the United States Patent and Trademark Office*